United States Patent
Jospa et al.

(10) Patent No.: US 6,520,578 B1
(45) Date of Patent: Feb. 18, 2003

(54) LABOR CHAIR

(76) Inventors: Erik Jospa, 1623 3rd Ave., Apt. 37-D, New York, NY (US) 10218; Gerald Jospa, 11 Tiana Pl., Dix Hills, NY (US) 11746

(*) Notice: Subject to any disclaimer, the term of this patent is extended or adjusted under 35 U.S.C. 154(b) by 0 days.

(21) Appl. No.: 09/573,408

(22) Filed: May 18, 2000

(51) Int. Cl.[7] .............. A47C 31/00; A47C 7/62
(52) U.S. Cl. .......... 297/217.1; 297/353; 297/383; 297/452.41; 297/452.13
(58) Field of Search .......... 297/452.41, 445.1, 297/383, 353, 452.13, 452.56, 217.1, DIG. 3

(56) References Cited

U.S. PATENT DOCUMENTS

| | | | | |
|---|---|---|---|---|
| 2,663,359 A | * | 12/1953 | Wood | 297/353 X |
| 2,942,651 A | * | 6/1960 | Binding | 297/353 X |
| 3,477,673 A | * | 11/1969 | Bereday | 297/353 X |
| 4,180,062 A | | 12/1979 | Alberti et al. | 128/698 |
| 4,703,671 A | | 11/1987 | Roberts et al. | 297/429 |
| 5,364,161 A | | 11/1994 | Liu | 297/195.11 |
| D353,460 S | | 12/1994 | Reynolds et al. | D24/183 |
| 5,558,400 A | * | 9/1996 | Poulson et al. | 297/353 X |
| 5,601,528 A | | 2/1997 | Mancarella | 601/45 |
| 5,690,389 A | | 11/1997 | Ekman et al. | 297/452.41 |
| 6,070,943 A | | 6/2000 | Guery-Strahm | 297/452.41 |

FOREIGN PATENT DOCUMENTS

| | | |
|---|---|---|
| DE | 9306731 | 10/1993 |
| DE | 29702389 | 6/1997 |
| DE | 9421950 | 8/1997 |
| DE | 20010364 | 11/2000 |
| SE | 679444 | 2/1992 |

OTHER PUBLICATIONS

Ball chair—www.balldynamics.com.

* cited by examiner

Primary Examiner—Rodney B. White
(74) Attorney, Agent, or Firm—Dilworth & Barrese, LLP

(57) ABSTRACT

A chair for a female in labor that includes a frame, and a ball for providing a seat for the female in labor. The frame includes a base, a back support member, and a horizontal moving assembly for movably adjusting the back support member horizontally relative to the base. The base includes a rim portion, a plate, and a pair of feet. The back support member includes a pair of feet, a pair of legs that have a pair of lower portions and a pair of upper portions, a transverse member, a plate with a throughslot, a back support assembly, and a vertical moving assembly for movably adjusting the back support assembly vertically relative to the upper portions of the pair of legs thereof. The back support assembly includes a cushion. The horizontal-moving assembly includes a pair of sleeves, and a pair of pins. The vertical moving assembly includes a threaded shaft, a pair of pins, and an internally threaded pin.

15 Claims, 3 Drawing Sheets

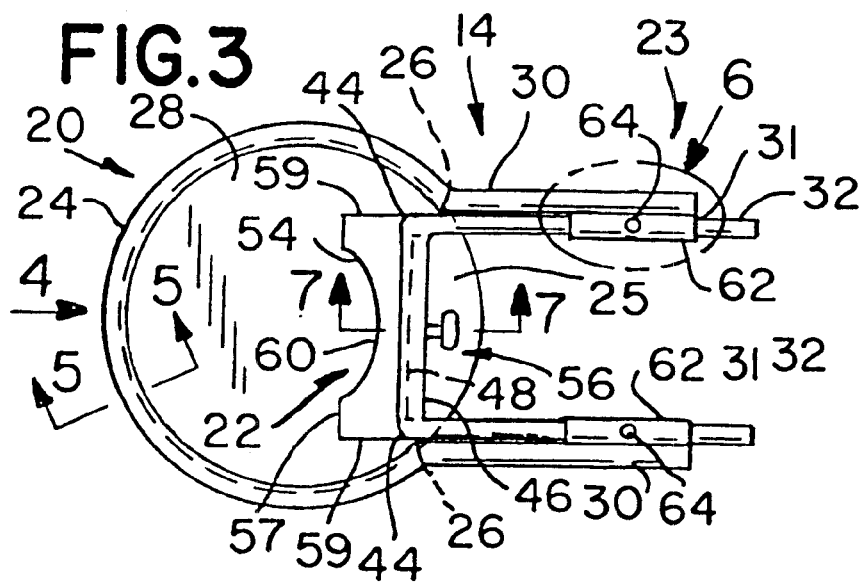
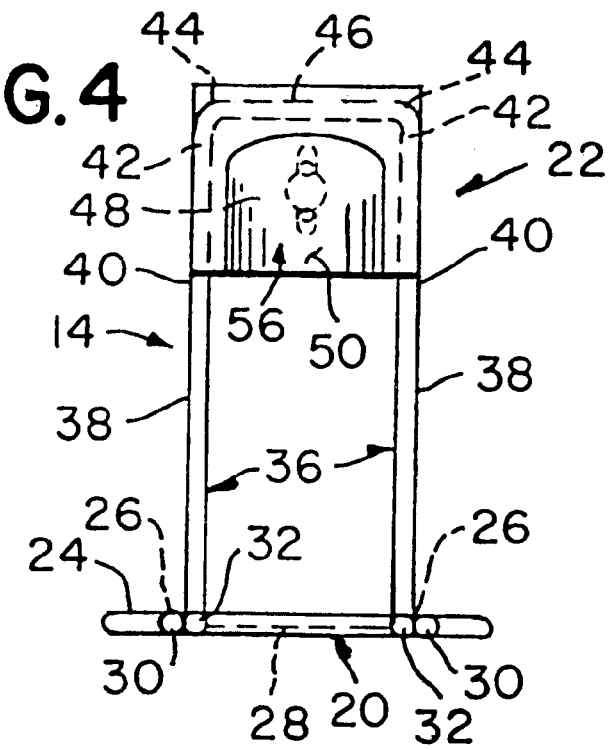

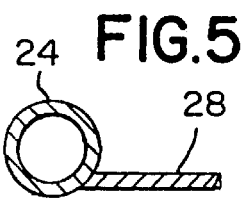
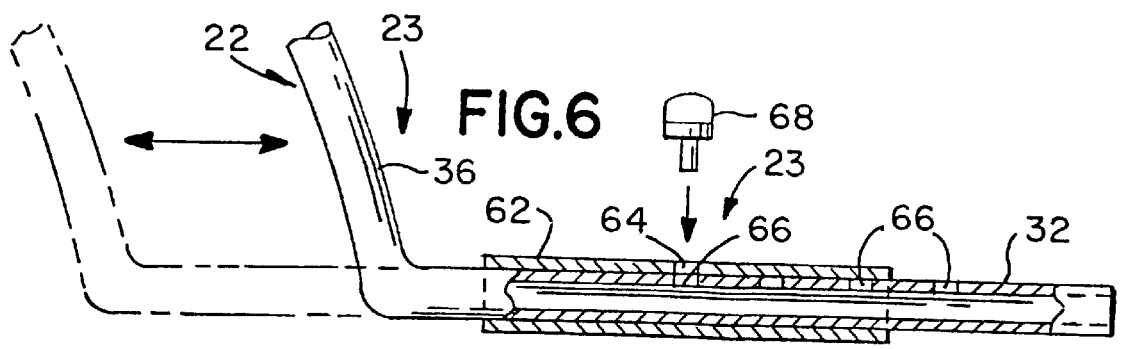
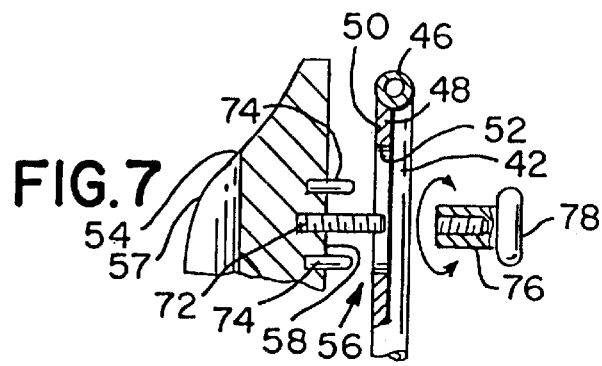

LABOR CHAIR

BACKGROUND OF THE INVENTION

1. Field of the Invention

The present invention relates to a chair. More particularly, the present invention relates to a labor chair.

2. Description of the Prior Art

Numerous innovations for chairs have been provided in the prior art that will be described. Even though these innovations may be suitable for the specific individual purposes to which they address, however, they differ from the present invention.

A FIRST EXAMPLE, U.S. Pat. No. Des. 353,460 to Reynolds et al. teaches the ornamental design for a labor chair.

A SECOND EXAMPLE, U.S. Pat. No. 4,180,062 to Alberti et al. teaches a portable childbirth chair including a base having a seat portion and two leg portions extending outwardly therefrom, two leg supports, each one being hingedly attached to a different one of the leg portions, two footrests each one being adjustably attached to a different one of the leg supports, adjustment straps for adjusting the inclination of the leg supports relative the base, a backrest hingedly attached to the seat portion, a back-rest support frame extending from the seat portion, and a pair of backrest adjustment rods pivotally attached to the backrest at one end and having other ends adapted to engage apertures formed along the backrest support frame so as to adjust the inclination of the backrest relative the base. The chair may be compactly collapsed for easy shipment and storage by telescoping the backrest support frame into the base, and folding the backrest and the two leg supports over the base. The chair also includes electronic monitoring apparatus.

A THIRD EXAMPLE, U.S. Pat. No. 4,703,975 to Roberts et al. teaches a labor chair for a pregnant woman to deliver her child. The labor chair comprises an essentially horizontal seat portion having a backrest, the seat portion being supported by a plurality of legs. An essentially planar work surface, having a footrest is selectively connected to the labor chair between the legs.

A FOURTH EXAMPLE, U.S. Pat. No. 5,364,161 to Liu teaches an inflatable rocking chair comprising a seat and a frame. The seat is inflatable having a holding portion and a sitting portion. The frame is formed from a plurality of tubes having two connecting tubes which forms the horizontal tubes of the chair. Two arch-shaped tubes contact the ground to provide, a rocking function of the chair. Two U-shaped tubes are used to connect the connecting tubes with the arch-shaped tubes so as to provide the frame and the inflatable seat as one unit. The frame of the inflatable chair is detachable.

A FIFTH EXAMPLE, U.S. Pat. No. 5,601,528 to Mancarella teaches an obstetric device that has two balloon or ring-shaped bodies of essentially identical design, which are positioned on an axis which runs in the horizontal direction when positioned for use, where the upper sections of the bodies are separated from one another by a gap which narrows in the downward direction and their top sides form a seat for a parturient sitting on the two bodies, and a pedestal-like base which can be positioned in an essentially stable, fixed spatial relationship to the bodies, and has footrests on which the feet of the parturient can be supported. In a preferred practical example, the pedestal-like base has a fluid-tight catch basin and a projection which reaches over and behind the bar connecting the bodies to one another. The obstetric device enables the parturient to assume a relaxed position during childbirth and a secure and gentle birth for the child to be born.

A SIXTH EXAMPLE, U.S. Pat. No. 5,690,389 to Ekman et al. teaches a chair having a large, inflated, ball-shaped seat. The ball-shaped seat of the chair re-forms in response to an individual's weight and his or her seated position. The ball-shaped seat's height is adjustable, so as to conform to differently-sized individuals. The deformable surface of the ball allows the spine of a seated individual to align itself. This activates the individual's trunk and back muscles, and makes comfortable and therapeutic seating possible for a wide variety of individuals, even those with back problems. The shell of the inflated ball can have a flexible, tough skin that is formed of rubber, plastic, leather or other air-impermeable material. For comfort and/or esthetic purposes, the shell can be covered with fabric or vinyl. Side handles can also be provided for comfort and stability. Additionally, casters can be provided for easy movement above the floor. Further, a back support can also be provided in order to maintain an individual's seated balance upon the ball.

It is apparent that numerous innovations for chairs have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a labor chair that avoids the disadvantages of the prior art.

ANOTHER OBJECT of the present invention is to provide a labor chair that is simple and inexpensive to manufacture.

STILL ANOTHER OBJECT of the present invention is to provide a labor chair that is simple to use.

BRIEFLY STATED, YET ANOTHER OBJECT of the present invention is to provide a chair for a female in labor that includes a frame, and a ball for providing a seat for the female in labor. The frame includes a base, a back support member, and a horizontal moving assembly for movably adjusting the back support member horizontally relative to the base. The base includes a rim portion, a plate, and a pair of feet. The back support member includes a pair of feet, a pair of legs that have a pair of lower portions and a pair of upper portions, a transverse member, a plate with a through slot, a back support assembly, and a vertical moving assembly for movably adjusting the back support assembly vertically relative to the upper portions of the pair of legs thereof. The back support assembly includes a cushion. The horizontal-moving assembly includes a pair of sleeves, and a pair of pins. The vertical moving assembly includes a threaded shaft, a pair of pins, and an internally threaded pin.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 3 is a diagrammatic top plan view taken generally in the direction of arrow 3 in FIG. 2;

FIG. 4 is a diagrammatic front elevational view taken generally in the direction of arrow 4 in FIG. 3;

FIG. 5 is an enlarged diagrammatic cross sectional view taken on line 5—5 in FIG. 4;

FIG. 6 is an enlarged diagrammatic side elevational view, in partial section, of the area generally enclosed by the dotted curve identified by arrow 6 in FIG. 3; and FIG. 7 is an enlarged diagrammatic cross sectional view taken on line 7—7 in FIG. 3.

Figure 1:
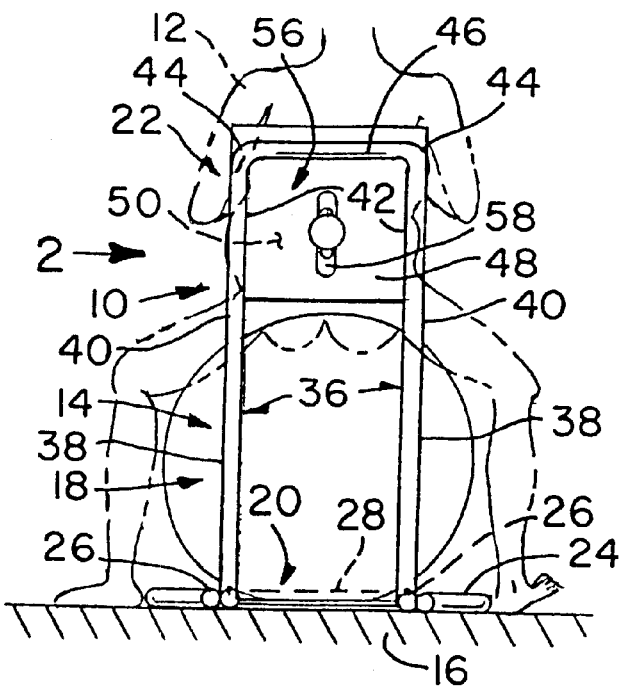
FIG. 1 is a diagrammatic rear elevational view of the present invention in use.
Figure 2:
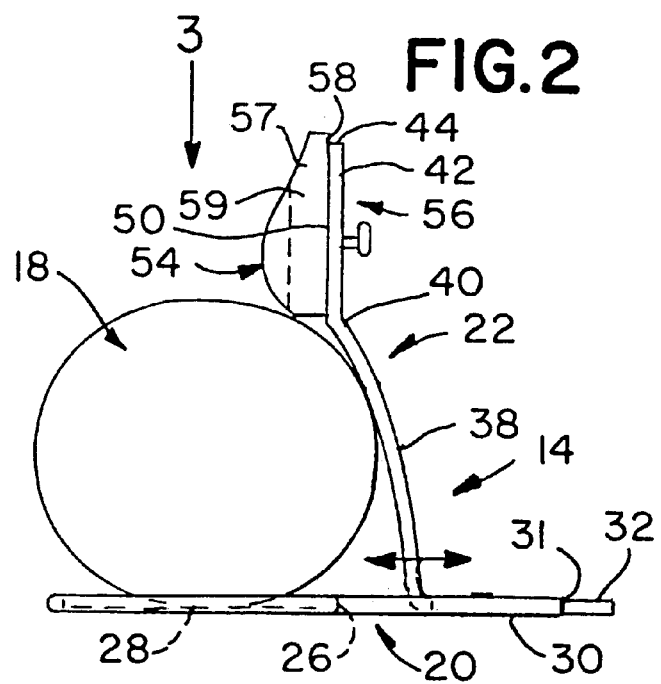
FIG. 2 is a diagrammatic side elevational view taken in the direction of arrow 2 in FIG. 1 of the present invention per se.

LIST OF REFERENCE NUMERALS UTILIZED IN THE DRAWING 10 chair of present invention for female in labor 12
12 female in labor
14 frame for resting on horizontal surface 16
16 horizontal surface
18 ball for providing a seat for female in labor 12
20 base of frame 14 for resting on horizontal surface 16
22 back support member of frame 14
23 horizontal moving assembly for adjusting for different sized females in labor 12
24 rim portion of base 20 of frame 14
25 open portion of rim portion 24 of base 20 of frame 14
26 pair of imaginary rearward-facing terminal ends defining open portion 25 of rim portion 24 of base 20 of frame 14
28 plate of base 20 of frame 14
30 pair of feet of base 20 of frame 14
31 pair of rearward-facing free terminal ends of pair of feet 30 of base 20 of frame 14
32 pair of feet of back support member 22 of frame 14
34 imaginary forward-facing terminal ends 34 of pair of feet 32 of back support member 22 of frame 14
36 pair of legs of back support member 22 of frame 14
38 pair of lower portions of pair of legs 36 of back support member 22 of frame 14
40 pair of upwardly-facing imaginary terminal ends of pair of lower portions 38 of pair of legs 36 of back support member 22 of frame 14
42 pair of upper portions of pair of legs 36 of back support member 22 of frame 14
44 pair of upwardly-facing imaginary terminal ends of pair of upper portions 42 of pair of legs 36 of back support member 22 of frame 14
46 transverse member of back support member 22 of frame 14
48 plate of back support member 22 of frame 14
50 forward-facing surface of plate 48 of back support member 22 of frame 14
52 through slot through plate 48 of back support member 22 of frame 14
54 back support assembly of back support member 22 of frame 14
56 vertical moving assembly for adjusting for different sized females in labor 12
57 cushion of back support assembly 54 of back support member 22 of frame 14
58 rearwardly-facing surface of cushion 57 of back support assembly 54 of back support member 22 of frame 14
59 pair of side surfaces of cushion 57 of back support assembly 54 of back support member 22 of frame 14
60 forwardly-facing surface of cushion 57 of back support assembly 54 of back support member 22 of frame 14
62 pair of sleeves of horizontal-moving assembly 23
64 pair of throughbores in pair of sleeves 62 of horizontal-moving assembly 23
66 plurality of throughbores of horizontal-moving assembly 23 in pair of feet 32 of back support member 22 of frame 14
68 pair of pins of horizontal-moving assembly 23
70 bulbous heads of pair of pins 68 of horizontal-moving assembly 23
72 threaded shaft of vertical moving assembly 56
74 pair of pins of vertical moving assembly 56
76 internally threaded pin of vertical moving assembly 56
78 bulbous head of internally threaded pin 76 of vertical moving assembly 56

DETAILED DESCRIPTION OF THE PREFERRED EMBODIMENT

Referring now to the figures, in which like numerals indicate like parts, and particularly to FIG. 1, the chair of the present invention is shown generally at 10 for a female in labor 12.

The overall configuration of the labor chair 10 can best be seen in FIG. 1, and as such, will be discussed with reference thereto.

The labor chair 10 comprises a frame 14 for resting on a horizontal surface 16, and a ball 18 that is operatively connected to the frame 14 for providing a seat for the female in labor 12.

The specific configuration of the frame 14 and its relationship to the ball 18 can best be seen in FIGS. 1–5, and as such, will be discussed with reference thereto.

The frame 14 comprises a base 20 that is stationary for resting on the horizontal surface 16, a back support member 22 that extends upwardly and movably from the base 20 of the frame 14, and a horizontal moving assembly 23 that movably attaches the back support member 22 of the frame 14 to the base 20 of the frame 14 for adjusting for different females in labor 12.

The base 20 of the frame 14 comprises a rim portion 24 that is horizontally-oriented, tubular, round, and substantially C-shaped with an open portion 25 that is defined by a pair of imaginary rearward-facing terminal ends 26.

The base 20 of the frame 14 further comprises a plate 28 that is horizontally-oriented, disc-shaped, fills the rim portion 24 of the base 20 of the frame 14, and provides a base and a lower vertical limit stop for the ball 18 to roll on, while the rim portion 24 of the base 20 of the frame 14 prevents the ball 18 from unintentionally rolling out of the base 20 of the frame 14.

The base 20 of the frame 14 further comprises a pair of feet 30 that are horizontally-oriented, tubular, straight, parallel to each other, and extend rearwardly from the pair of rearward-facing imaginary terminal ends 26, of, and are coplanar with, the rim portion 24 of the base 20 of the frame 15, respectively, to a pair of rearward-facing free terminal ends 31.

The back support member 22 of the frame 14 comprises a pair of feet 32 that are horizontally-oriented, tubular, straight, parallel to each other, and horizontally-movably attached to the pair of feet 30 of the base 20 of the frame 14, respectively, by way of the horizontal-moving assembly 23, so as to allow front and back adjustment of the back support member 22 of the frame 14 relative to the base 20 of the frame 14 for adjusting for different sized females in labor 12, and have a pair of imaginary forward-facing terminal ends 34.

The back support member 22 of the frame 14 further comprises a pair of legs 36 that are tubular and parallel to each other.

The pair of legs 36 of the back support member 22 of the frame 14 have a pair of lower portions 38 that extend upwardly and arcutely forwardly from the pair of imaginary forward-facing terminal ends 34 of the pair of feet 32 of the back support member 22 of the frame 14, respectively, provide a rear horizontal limit stop for the ball 18, and have a pair of upwardly-facing imaginary terminal ends 40.

The pair of legs 36 of the back support member 22 of the frame 14 further have a pair of upper portions 42 that extend upwardly and straight from the pair of imaginary upward-facing terminal ends 40 of the pair of lower portions 38 of the pair of legs 36 of the back support member 22 of the frame 14, respectively, and have a pair of upwardly-facing imaginary terminal ends 44.

The back support member 22 of the frame 14 further has a transverse member 46 that is tubular, horizontally-oriented, straight, and extends transversely from one terminal end of the pair of upwardly-facing imaginary terminal ends 44 of the pair of upper portions 42 of the pair of legs 36 of the back support member 22 of the frame 14, to the other terminal end of the pair of upwardly-facing imaginary terminal ends 44 of the pair of upper portions 42 of the pair of legs 36 of the back support member 22 of the frame 14.

The back support member 22 of the frame 14 further has a plate 48 that is vertically-oriented and extends transversely from one upper portion of the pair of upper portions 42 of the pair of legs 36 of the back support member 22 of the frame 14, to the other upper portion of the pair of upper portions 42 of the pair of legs 36 of the back support member 22 of the frame 14, and depends from the transverse member 46 of the back support member 22 of the frame 14, to the pair of imaginary upward-facing terminal ends 40 of the pair of lower portions 38 of the pair of legs 36 of the back support 22 of the frame 14.

The plate 48 of the back support member 22 of the frame 14 has a forward-facing surface 50, and a through slot 52 that extends vertically and centrally therethrough.

The back support member 22 of the frame 14 further has a back support assembly 54 that is vertically movably attached to the forward-facing surface 50 of the plate 48 of the back support member 22 of the frame 14, by way of a vertical moving assembly 56, so as to allow up and down adjustment of the back support assembly 54 of the back support member 22 of the frame 14 relative to the plate 48 of the back support member 22 of the frame 14 for adjusting for different sized females in labor 12.

The back support assembly 54 of the back support member 22 of the frame 14 has a cushion 57 that extends transversely from one upper portion of the pair of upper portions 42 of the pair of legs 36 of the back support member 22 of the frame 14, to the other upper portion of the pair of upper portions 42 of the pair of legs 36 of the back support member 22 of the frame 14, and depends from the transverse member 46 of the back support member 22 of the frame 14, to the pair of imaginary upward-facing terminal ends 40 of the pair of lower portions 38 of the pair of legs 36 of the back support member 22 of the frame 14.

The cushion 57 of the back support assembly 54 of the back support member 22 of the frame 14 has a rearwardly-facing surface 58 that is flat and movably attached to the forward-facing surface 50 of the plate 48 of the back support member 22 of the frame 14, a pair of side surfaces 59 that extend forwardly from the rearwardly-facing surface 58 thereof, over, and provide an upper vertical limit stop for, the ball 18, and a forwardly facing surface 60 that extends transversely from one side surface of the pair of side surfaces 59 thereof to the other side surface of the pair of side surfaces 59 thereof.

The forward-facing surface 60 of the cushion 57 of the back support assembly 54 of the back support member 22 of the frame 14 is ergonomically-shaped and is concave in plan view and serpentine in side view, starting in a concave shape and then depending therefrom to a convex shape for providing comfort for the back of the female in labor 12.

The specific configuration of the horizontal-moving assembly 23 can best be seen in FIGS. 3 and 6, and as such, will be discussed with reference thereto.

The horizontal-moving assembly 23 comprises a pair of sleeves 62 that are tubular, straight, horizontally-oriented, parallel to each other, face each other, and extend axially along, and inboard of, the pair of feet 30 of the base 20 of the frame 14, respectively, from flush with the pair of rearward facing free terminal ends 31 of the pair of feet 30 of the base 20 of the frame 14, to approximately midway of the pair of feet 30 of the base 20 of the frame 14, respectively, and horizontally slidingly receive the pair of feet 32 of the back support member 22 of the frame 14, respectively.

The pair of sleeves 62 of the horizontal-moving assembly 23 have a pair of throughbores 64 that extend centrally through uppermost surfaces thereof, respectively.

The horizontal-moving assembly 23 further comprises the pair of feet 32 of the back support member 22 of the frame 14 having a plurality of throughbores 66 extending through upper surfaces thereof, respectively, each of which being alignable with the pair of throughbores 64 in the pair of sleeves 62 of the horizontal 2 moving assembly 23, respectively.

The horizontal-moving assembly 23 further comprises a pair of pins 68 that have bulbous heads 70, and which pass through the pair of throughbores 64 in the pair of sleeves 62 of the horizontal-moving assembly 23, respectively, and into an aligned pair of throughbores of the plurality of throughbores 66 in the pair of feet 32 of the back support member 22 of the frame 14, respectively, once adjusted, while the bulbous heads 70 of the pair of pins 68 of the horizontal-moving assembly 23 provide a limit stop therefor.

The specific configuration of the vertical moving assembly 56 can best be seen in FIG. 7, and as such, will be discussed with reference thereto.

The vertical moving assembly 56 comprises a threaded shaft 72 that is horizontally-oriented, extends rearwardly and centrally from the rearwardly-facing surface 58 of the cushion 57 of the back support assembly 54 of the back support member 22 of the frame 14, and vertically movably through the through slot 52 in the plate 48 of the back support member 22 of the frame 14.

The vertical moving assembly 56 further comprises a pair of pins 74 that are horizontally-oriented, parallel to each other and to the threaded shaft 72 of the vertical moving assembly 56, extend rearwardly from the rearwardly-facing surface 58 of the cushion 57 of the back support assembly 54 of the back support member 22 of the frame 14, vertically straddle, with shorter lengths than, the threaded shaft 72 of the vertical moving assembly 56, and through the through slot 52 in the plate 48 of the back support member 22 of the frame 14 so as to limit the up and down movement of the threaded shaft 72 of the vertical moving assembly 56.

The vertical moving assembly 56 further comprises an internally threaded pin 76 that threadably receives the threaded shaft 72 of the vertical moving assembly 56 after the threaded shaft 72 of the vertical moving assembly 56 has passed through the plate 48 of the back support member 22 of the frame 14, and when tightened, locks the cushion 57 of the back support assembly 54 of the back support member 22 of the frame 14 at a desired height.

The internally threaded pin 76 of the vertical moving assembly 56 has a bulbous head 78 to facilitate turning.

It will be understood that each of the elements described above, or two or more together, may also find a useful application in other types of constructions differing from the types described above.

While the invention has been illustrated and described as embodied in a labor chair, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A chair comprising a support and a base having an upper portion, a lower portion, and a pair of surfaces interconnecting said upper and lower portions, said lower portion defining a plane configured to be in direct contact with a surface and further defining an opening through to said surface, and a rim portion extending substantially along a periphery of said lower portion, wherein said support is attached to said base and extends substantially upwardly from said plane, said base and said support collectively defining a receiving area configured to receive an elastic seating member therein such that said elastic seating member contacts said surface through said opening in said lower portion, said elastic seating member being configured and adapted such that a downward pressure acting on said elastic seating member will cause said elastic seating member to deflect and contact at least a portion of said rim in order to stabilize said base on said surface, wherein said base is at least partially circular in shape and further includes a pair of substantially parallel base feet that extend horizontally from said base.

2. A chair as in claim 1, wherein said base is at least partially tubular in cross-section.

3. A chair comprising:
    a base having an upper portion, a lower portion, and a pair of surfaces interconnecting said upper and lower portions, said lower portion defining a plane configured to be in direct contact with a horizontal surface, and wherein said base further includes a pair of substantially parallel base feet that extend horizontally from said base; and
    a support including a pair of support feet disposed adjacent to said base feet for slidable engagement therewith; wherein said support is attached to said base and extends substantially upwardly from said plane, said base and said support collectively defining a receiving area configured to accommodate an elastic seating member.

4. A chair as in claim 1, wherein said support includes a back support assembly.

5. A chair as in claim 4, wherein said back support assembly is vertically adjustable relative to said base.

6. A chair as in claim 4, wherein said back support assembly is configured to at least partially conform to a human anatomical feature.

7. A chair as in claim 1, wherein said chair includes an elastic seating member disposed in said receiving area defined by said base and said support.

8. A chair as in claim 7, wherein said base is configured to at least partially contact a surface of said elastic seating member when said elastic seating member is deformed under a predetermined load.

9. A chair as in claim 7, wherein said elastic seating member is an inflated ball.

10. A chair comprising a support having a pair of support feet, a base having an upper portion, a lower portion, at least one surface interconnecting said upper and lower portions and a pair of base feet, said lower portion and said base feet defining a plane configured to be in direct contact with a horizontal surface, said pair of support feet and said pair of base feet extending substantially parallel along said plane and functioning to interconnect said base adjacent said support, said base and said support collectively defining a receiving area configured to accommodate an elastic seating member.

11. A chair as in claim 10, wherein said chair includes a ball forming said elastic seating member.

12. A chair as in claim 10, wherein said base is substantially circular with at least one opening in said at least one surface, said opening at least partially defined by said base feet.

13. A chair as in claim 10, wherein said support is substantially U-shaped.

14. A chair as in claim 10, wherein said support further includes an anatomical support assembly.

15. A chair as in claim 1, wherein said support is adjustable relative to said base.

* * * * *